(12) United States Patent
Magee et al.

(10) Patent No.: US 8,563,048 B2
(45) Date of Patent: *Oct. 22, 2013

(54) BOTANICAL BUTTER STICK LIP BALM

(75) Inventors: Sara Vest Magee, Glen Allen, VA (US); John Oliver Bachert, Richmond, VA (US); Neil Partridge, Mechanicsville, VA (US); Jay Roberts Dickerson, Midlothian, VA (US)

(73) Assignee: Wyeth LLC, Madison, NJ (US)

( * ) Notice: Subject to any disclaimer, the term of this patent is extended or adjusted under 35 U.S.C. 154(b) by 413 days.

This patent is subject to a terminal disclaimer.

(21) Appl. No.: 12/711,704

(22) Filed: Feb. 24, 2010

(65) Prior Publication Data

US 2010/0151060 A1 Jun. 17, 2010

Related U.S. Application Data

(63) Continuation of application No. 11/904,927, filed on Sep. 28, 2007, now Pat. No. 7,695,727.

(60) Provisional application No. 60/850,724, filed on Oct. 11, 2006.

(51) Int. Cl.
*A61K 8/02* (2006.01)
*A61K 36/00* (2006.01)
*A61Q 1/04* (2006.01)

(52) U.S. Cl.
USPC .......................... 424/725; 424/64; 424/401

(58) Field of Classification Search
USPC ........................................ 424/64, 401, 725
See application file for complete search history.

(56) References Cited

U.S. PATENT DOCUMENTS

| | | | |
|---|---|---|---|
| 5,780,018 A | 7/1998 | Collins et al. | |
| 6,063,391 A | 5/2000 | Nanba et al. | |
| 6,358,498 B1 | 3/2002 | Yu et al. | |
| 6,586,018 B1 | 7/2003 | Fasano | |
| 6,800,292 B1 | 10/2004 | Murad | |
| 2003/0082218 A1 | 5/2003 | Ichinohe et al. | |
| 2004/0007284 A1 | 1/2004 | Look et al. | |
| 2004/0028641 A1* | 2/2004 | Barone et al. | 424/74 |
| 2004/0180020 A1 | 9/2004 | Manelski et al. | |
| 2004/0223990 A1 | 11/2004 | Mondet et al. | |
| 2005/0207999 A1* | 9/2005 | Vernaire et al. | 424/59 |
| 2005/0271692 A1 | 12/2005 | Gervasio-Nugent et al. | |
| 2005/0276770 A1 | 12/2005 | Filippi et al. | |
| 2006/0013789 A1 | 1/2006 | Blin et al. | |

FOREIGN PATENT DOCUMENTS

| | | |
|---|---|---|
| EP | 0919225 A2 | 6/1999 |
| EP | 1314415 A1 | 5/2003 |
| WO | WO 03/011234 A1 | 2/2003 |
| WO | WO 03/068176 A1 | 8/2003 |
| WO | WO 04/000242 A1 | 12/2003 |
| WO | WO 2004/024105 A1 | 3/2004 |
| WO | WO 2007/022141 A1 | 2/2007 |

OTHER PUBLICATIONS

Beeswax Lip Balm, webpage from burtsbees.com, Sep. 2006.
PCT/US2007/021667—International search Report, Mailed Feb. 27, 2008.

* cited by examiner

*Primary Examiner* — Gina C Justice

(74) *Attorney, Agent, or Firm* — Jeffrey Gold; Joseph F. Reidy

(57) ABSTRACT

A stick lip balm with efficacious amounts of natural moisturizer and organoleptic/sensory attributes of lip feel associated with moisturizers and emollients is provided. The lip balm of the invention comprises at least 90% botanically derived materials and can be formed into a stick sufficiently robust to substantially retain the stick shape under normal conditions of shipping, storage and usage. A method of making the stick lip balm is also provided.

18 Claims, No Drawings

BOTANICAL BUTTER STICK LIP BALM

This continuation of copending U.S. application Ser. No. 11/904,927 filed on Sep. 28, 2007 which claims benefit to U.S. Provisional Application No. 60/850,724 filed Oct. 11, 2006, the entire disclosure of each of which is incorporated herein by reference.

FIELD OF INVENTION

A stick lip balm comprising botanical extract butters is provided.

BACKGROUND OF THE INVENTION

Many lip balms are commercially available in a stick form. Conventional stick lip balms typically contain a large amount of wax, e.g. amounts of conventional waxes in excess of 20% wt/wt of the composition. Waxes are used in the composition to give the composition sufficient structure to maintain a stick form under shipping and normal use conditions. Petroleum derived waxes such as ozokerite, paraffin, and microcrystalline petroleum based waxes are commonly used as they provide a robust stick structure and are relatively inexpensive materials.

As lips are the area of application, many users prefer the use of a "natural" product and consider petroleum-derived waxes to be synthetic products. Accordingly, use of "natural" waxes such as beeswax or plant derived waxes such as candelilla or carnauba have in some instances been used instead of or as a partial replacement for petroleum wax. While use of only botanically derived candelilla or carnauba wax may appeal to consumers, the use of only those two waxes either separately or in combination may lead to shrinkage problems when a lip balm stick is formed which in some instances may yield a stick with deformed portions.

Not only does the wax contribute significantly to the structure of the stick but also it provides the benefit of forming a protective layer when applied to the lips. Conventional stick lip balms formed using the conventional petroleum derived base waxes discussed above, while having protective properties, may not replenish natural lip lipids as well as naturally derived lipids and thus may not maintain natural moisture balance and prevent drying, chapping and cracking of lips.

Natural moisturizing lip balm products are available commercially, but typical commercially available moisturizing products with significant amounts of moisturizing ingredients are too soft to form a stick that can withstand storage, shipment and/or application to the lips without significant distortion of shape. Thus, natural moisturizing lip balm compositions are usually sold in tubes or pots and application is accomplished at least in part by the user's fingers. Thus application is messy, and particularly inconvenient if hand-washing facilities are not immediately available.

Accordingly, it would be desirable to have a natural stick lip balm product with efficacious amounts of natural moisturizer.

SUMMARY OF THE INVENTION

The invention provides a stick lip balm comprising a carnauba wax; a canedelilla wax; jojoba esters; a plurality of botanical butters; and at least one additional moisturizing agent. The non-jojoba ester waxes comprise less than about 20% of the composition and at least 90% of the composition is derived from botanical sources. Any non-botanical components are free of materials derived from mammalian sources and petroleum sources.

The composition may further comprise one or more of an antioxidant, a flavorant, a sensate, a beneficial agent and/or an additional moisturizing agent.

The invention provides a method for manufacturing a stick lip balm comprising forming a molten composition of a carnauba wax, jojoba esters and at least one additional moisturizing agent wherein the total amount of non-jojoba wax is less than 20% of the stick lip balm composition. The molten composition is combined with a plurality of botanical butters. The molten composition with botanical butters is filled into a stick forming container; and the molten composition is cooled in the stick forming container to a temperature to form a solid stick. The stick forming container may be a dispensing tube or alternatively a mold.

DETAILED DESCRIPTION OF THE INVENTION

A stick lip balm with efficacious amounts of natural moisturizer and organoleptic/sensory attributes of lip feel associated with moisturizers and emollients is provided. The lip balm of the invention can be formed into a stick sufficiently robust to substantially retain the stick shape under normal conditions of shipping, storage and usage.

The lip balm contains all natural, non-mammalian ingredients with greater than about 90% of the composition derived from botanical sources. The composition includes a plurality of natural butter ingredients which are compositions having emollient properties. The composition further comprises moisturizing agents such as coconut oil, jojoba esters, and sunflower seed oil, for example. The composition comprises less than 20% conventional waxes. Optionally, the composition may contain one or more antioxidants, but preferably does not include preservatives.

As used herein, a "butter" or "botanical butter" is a fat and/or oil extract of a plant fruit and/or seed characterized by having emollient properties and a melting point near human body temperature. As used herein "butter" has the meaning as defined and is distinguished from a conventional wax and/or a non-jojoba ester. A butter includes both pure extracts from a plant fruit or seed and/or extract from a plant fruit or seed combined with additional lipid material to achieve the melting point characteristic and/or lubricity. Preferably the lipid material is derived from a botanical source. Exemplary butters include, but are not limited to, mango seed butter, raspberry butter, avocado butter, shea butter, olive butter, kuku butter, monoi butter, peach butter, pistachio butter, coconut butter, cocoa butter, pomegranate butter, rose hip butter, sunflower butter, wheat germ butter, apricot butter, babassu butter, cupuacu butter, kokum butter, hazelnut butter, jojoba butter, sesame butter, soy butter, almond butter, meadowfoam seed butter, black current seed butter and cranberry butter.

The terms "about" or "approximately" mean within an acceptable range for the particular parameter specified as determined by one of ordinary skill in the art, which will depend, in part, on how the value is measured or determined, e.g. the limitations of the measurement system. For example, "about" can mean a range of up to 10% of a given value.

"Percent" or "%" as used herein refers to the percentage by weight of the total composition, unless otherwise specified.

An "emollient" is a cosmetic ingredient which can help maintain the soft, smooth and pliable appearance of skin tissue. Typically, emollients impart sensory properties of smoothness and/or softness when the composition is applied to the lips.

"Conventional wax" or "conventional waxes" include petroleum derived waxes, beeswax, carnauba wax and candelilla wax. These waxes may also be referred to herein as "non-jojoba wax" or "non-jojoba waxes". Jojoba waxes are distinguishable from conventional waxes in that they are derived from the jojoba plant and they have properties that contribute to structure as well as providing substantial emollient and moisturizing properties not characteristic of conventional waxes.

A "lip balm" is a semisolid composition for application to the lips that has protective and/or moisturizing properties. Optionally, lip balms may contain medicaments and/or ingredients that promote lip health such as, for example, sunscreens. Lip balms may be colored but unlike lipsticks do not impart a color to the lips. A "stick lip balm" is a lip balm formed into a stick shape that is typically dispensed from a container that permits extension of the lip balm stick from the container and retraction of the lip balm stick back into the container, In an exemplary embodiment of the invention, a combination of non-mammalian waxes including beeswax, carnauba wax and candelilla wax is combined with a plurality of jobjoba esters, a plurality of butters and sunflower seed oil to form a composition that has a rich, soft, smooth feel when applied to the lips, moisturizing properties and sufficient structure as a composition to form a stick with sufficient robustness for commercial use. The amount of conventional wax e.g. beeswax, carnauba and candelilla is preferably less than 20% of the total composition with the amount of beeswax preferably less than 5% of the total composition. Conventional waxes, particularly beeswax while useful for imparting structural support, also impart a rigidity that does not favorably contribute to a rich, soft, smooth lip feel. Hence, it is preferable to minimize the use of beeswax in the composition. The use of waxes from petroleum or mammalian sources is preferably avoided. In one embodiment the conventional waxes used consist essentially of botanically derived waxes in an amount of less than about 15% and beeswax in an amount of less than about 5%.

To obtain both the emollient properties and desired structure a mixture of jojoba esters is used. Jojoba esters are lipid esters derived from Jojoba plants. Depending on the size and structure of a given ester, the physical properties may range form waxy to oily. In view of commercially available jojoba ester products such as Floraesters supplied by FloraTech Americas, 1151 North Fiesta Blvd., Gilbert, Ariz. 85233, it may be convenient to use a combination of jojoba ester products. For example, in an exemplary embodiment a mixed jojoba ester product with a melting point range of 47-51° C. was used in combination with a mixed jojoba ester product having a melting point range of 56-61° C. Typically, the total amount of jojoba ester is about 5% to about 50% of the total composition.

The composition comprises a plurality of botanical butters. Generally butters contribute skin-conditioning properties to the composition. A plurality of butters is desirable as, in addition to emollient and moisturizing properties, these naturally derived substances have a variety of other attributes depending on the botanical source of the butter. For example, butters may vary in their sensory feel and/or have particular components with desired functionalities such as components that enhance lip barrier function, enhance penetration, or have antioxidant properties or the like. Accordingly, a combination of butters provides for modulation of lip feel (such as, for example, suppleness and/or moistness) of the composition as well as a source of natural ingredients with beneficial attributes (such as, for example, emollient, moisturizer, medicament, and/or antioxidant).

Preferably the composition comprises at least two butters and more preferably three or more butters. Suitable butters include but are not limited to mango seed butter, raspberry butter, avocado butter, shea butter, olive butter, kuku butter, monoi butter, peach butter, pistachio butter, coconut butter, cocoa butter, pomegranate butter, rose hip butter, sunflower butter, wheat germ butter, apricot butter, babassu butter, cupuacu butter, kokum butter, hazelnut butter, jojoba butter, sesame butter, soy butter, almond butter, meadowfoam seed butter, black current seed butter, cranberry butter and combinatios thereof. Depending on the total number of butters used the total amount of butter is typically about 2% to about 20%.

The composition further comprises moisturizing oils. Exemplary oils suitable for use in the composition included, but are not limited to, sunflower oil, coconut oil, castor oil, vegetable oil, corn oil, aloe vera oil, canola oil, soybean oil, jojoba oil, olive oil, babassu oil, avocado oil, apricot oil, meadowfoam seed oil, macademia seed oil, oat kernel oil, palm seed oil, safflower oil, sandalwood oil, sesame oil, almond oil, wheat germ oil, cranberry oil and combinations thereof. In view of consumer preferences it is preferable to use an oil from a botanical source. Oils may be included in the composition in amounts of about 5% to about 65%.

The composition may further comprise one or more antioxidants. Antioxidants may protect the composition from oxidation (e.g. becoming rancid) and/or provide lip conditioning benefits upon application to the lips. In view of consumer preferences for "natural" products natural antioxidants such as tocopherols are preferred. Tocopherols, tocopheryl acetate, some botanical butters and green tea extracts are exemplary antioxidants suitable for use in the composition.

Optionally, the composition may further comprise a flavorant. In view of consumer preferences it is preferable to use a natural flavorant material. Flavorants are typically used in amounts of about 0.1% to 5%. Amounts may vary depending on the potency of the flavorant and matrix in which the flavorant is presented. Flavorants may be presented in a botanical lipid matrix, for example.

Optionally, the composition may further comprise natural medicaments including, but not limited to, menthol, camphor, eucalyptus, salicylic acid, and derivatives of salicylic acid. Typically medicaments would be added in amounts of less than about 3%. Amounts may vary depending on the potency of the medicament and the matrix in which the medicament is presented.

Optionally, colorant that imparts color to the composition may be included in the composition. The colorant should not be of an amount, particle size, and/or presented in a matrix that would permit transfer of colorant that imparts a color to the lips during application. Natural colorants such as, for example, plant extracts, natural minerals, or carmine are preferred.

Optionally, a sensate may be included in the composition. A sensate is a composition that initiates a sensory perception such as heating or cooling, for example, when contacted with the skin and/or lips. Exemplary sensates include, but are not limited to, mint extracts, cinnamon extract, and capsaicin. Preferably sensates are derived from natural sources. However, as sensates typically have high potency and accordingly may yield significant impact at low levels, synthetic sensates are within the scope of this invention.

Other beneficial agents known to one skilled in the art may likewise optionally be included in the composition. Aloe extracts and natural organic acids are exemplary of other beneficial agents. Natural organic acids including α-hydroxy acids may act as exfoliants, for example. Lactic acid is an exemplary α-hydroxy acid. Preferably any other beneficial agents are derived from botanical sources.

The composition of the invention may be prepared as a molten liquid mixture and poured into containers that form the stick shape as the molten mixture cools to a semi-solid state. In one embodiment, the non-jojoba esters are heated sufficiently to form a molten composition and then combined with the jojoba esters with mixing. As over heating may be detrimental to some butters, the temperature of the molten mixture is reduced and/or adjusted to not exceed 160° F. prior to the addition of the butters. Preferably the temperature of the mixture is held in the range of 140-160° F. during any additional mixing steps subsequent to the addition of the butters. Additional mixing steps may include, for example, addition of antioxidants and/or flavorants.

Upon combination of all ingredients, the molten composition is placed in a stick forming container or containers and allowed to solidify. Optionally, once placed in the container, the forming stick may be subjected to a one or more heating and cooling cycles as it solidifies to optimize formation of the stick. Optionally, the stick-forming container may be a dispensing tube.

Alternatively, the molten composition may be filled into a mold and allowed to solidify in the mold to form a stick. Once formed, the stick is removed from the mold and placed in a dispensing container.

Typically, suitable dispensing containers comprise an elevator portion which permits extending the stick from the dispensing container to facilitate application to the user's lips and retraction of the stick back into the container for storage.

Example 1

An exemplary composition comprising five botanical butters is provided in Table 1. This composition is representative and one of many composition that are within the scope of the invention. The exemplary embodiment is provided for illustrative purposes.

TABLE 1

| Ingredient | Amount % wt/wt |
| --- | --- |
| Yellow Beeswax | 3.50 |
| Shea butter | 0.75 |
| Coconut oil | 10.75 |
| Carnuauba wax | 1.25 |
| Candelilla wax | 13 |
| Flavorant | 4 |
| Mango butter | 0.75 |
| Tocopheryl acetate | 1 |
| Tocopherol | 0.2 |
| Avacodo butter | 0.75 |
| Jojoba esters (mp 56-61° C.) | 8 |
| Jojoba esters (mp 47-51° C.) | 11 |
| Olive butter | 0.75 |
| Raspberry butter | 0.75 |
| Sunflower seed oil | 43.55 |

The composition of Table 1 may be prepared by combining the carnauba wax, candelilla wax, beeswax and coconut oil with mixing and heating in the range of 175-190° F. Upon formation of a molten mixture the temperature may be reduced to 155-170° F. and the jojoba esters added with mixing. Upon complete mixing the temperature may be reduced to 120-139° F. and the sunflower oil added with mixing. The temperature may then be adjusted to 140-160° F. and the butters added with mixing. Upon completion of addition of the butters, tocopherol, tocopheryl acetate and flavorant may be added with mixing.

The molten mixture thus formed may be directly dispensed into dispensing tubes, or alternatively, dispensed into stick forming molds and cooled to solidify and then placed in dispensing tubes Although the foregoing invention has been described in some detail by way of illustrations and examples for purposes of clarity of understanding, it will be obvious that certain changes and modifications may be practiced within the scope of the appended claims. Modifications of the above-described modes of practicing the invention that are obvious to persons of skill in the art are intended to be included within the scope of the following claims.

What is claimed is:
1. A stick lip balm comprising:
  (i) a carnauba wax;
  (ii) a candelilla wax;
  (iii) jojoba esters wherein the jojoba esters comprise a first jojoba ester having a melting point of about 47° C. to about 51° C. and a second jojoba ester having a melting point of about 56° C. to about 61° C.;
  (iv) at least two botanical butters; and
at least one additional moisturizing agent, wherein non-jojoba ester waxes comprise less than about 20% of the composition and wherein at least 90% of the composition is derived from botanical sources and any non-botanical components are free of materials derived from mammalian sources and petroleum sources.

2. The composition of claim 1 further comprising an antioxidant.

3. The composition of claim 2 wherein the antioxidant is tocopherol.

4. The composition of claim 1 wherein the plurality of botanical butters is selected from the group consisting of mango seed butter, raspberry butter, avocado butter, shea butter, olive butter, kuku butter, monoi butter, peach butter, pistachio butter, coconut butter, cocoa butter, pomegranate butter, rose hip butter, sunflower butter, wheat germ butter, apricot butter, babassu butter, cupuacu butter, kokum butter, hazelnut butter, jojoba butter, sesame butter, soy butter, almond butter, meadowfoam seed butter, black current seed butter, cranberry butter and combinations thereof.

5. The composition of claim 1 wherein the plurality of botanical butters includes at least three butters.

6. The composition of claim 1 further comprising a flavorant.

7. The composition of claim 1 further comprising aloe leaf extract.

8. The composition of claim 1 further comprising less than 5% beeswax.

9. The composition of claim 1 further comprising a medicament.

10. The composition of claim 1 further comprising a sensate.

11. The composition of claim 1, wherein the at least one additional moisturizing agent is selected from the group consisting of sunflower oil, coconut oil, castor oil, vegetable oil, corn oil, aloe vera oil, canola oil, soybean oil, jojoba oil, olive oil, babassu oil, avocado oil, apricot oil, meadowfoam seed oil, macadamia seed oil, oat kernel oil, palm seed oil, safflower oil, sandalwood oil, sesame oil, almond oil, wheat germ oil, cranberry oil, and combinations thereof.

12. The composition of claim 11, wherein the at least one additional moisturizing agent is a combination of coconut oil and sunflower oil.

13. A method for manufacturing a stick lip balm comprising: forming a molten composition of a carnauba wax, jojoba esters and at least one additional moisturizing agent wherein the total amount of non-jojoba wax is less than 20% of the stick lip balm, wherein the jojoba esters comprise a first jojoba ester having a melting point of about 47° C. to about 51° C. and a second jojoba ester portion having a melting point of about 56° C. to about 61° C.;
   combining the molten composition with at least two botanical butters;
   filling the molten composition into a stick forming container; and
   cooling the molten composition in the stick forming container to a temperature to form a solid stick.

14. The method of claim 13, further comprising maintaining the temperature of the molten composition at or below about 160° F. when the plurality of butters are present in the composition.

15. The method of claim 13, wherein the stick-forming container is a dispensing tube.

16. The method of claim 13, wherein the stick-forming container is a mold.

17. The method of claim 16, further comprising removing the solid stick from the mold.

18. The method of claim 17, further comprising placing the solid stick in a dispensing tube.

\* \* \* \* \*